United States Patent [19]

Ewall

[11] Patent Number: 4,977,892
[45] Date of Patent: Dec. 18, 1990

[54] WOUND DRESSING WITH HYDROPHILIC ABSORBENT LAYER

[75] Inventor: Ralph X. Ewall, Chagrin Falls, Ohio

[73] Assignee: The B. F. Goodrich Company, Akron, Ohio

[21] Appl. No.: 430,903

[22] Filed: Oct. 3, 1989

Related U.S. Application Data

[63] Continuation of Ser. No. 89,204, Aug. 25, 1987, abandoned, which is a continuation-in-part of Ser. No. 899,575, Aug. 25, 1986, abandoned.

[51] Int. Cl.$^5$ ............... A61F 13/00; A61F 15/00; A61L 15/00
[52] U.S. Cl. .................. 128/156; 128/155; 604/307; 604/364; 523/105
[58] Field of Search ............... 128/155, 156; 604/304, 604/307, 358, 365, 365, 372, 384; 428/254; 523/105, 111

[56] References Cited

U.S. PATENT DOCUMENTS

| | | | |
|---|---|---|---|
| 3,632,416 | 1/1972 | Shepherd et al. | 128/156 |
| 3,842,832 | 10/1974 | Wideman et al. | 128/156 |
| 3,949,130 | 4/1976 | Sabee et al. | 604/365 |
| 4,062,817 | 12/1977 | Westerman | 526/206 |
| 4,066,583 | 1/1978 | Spaulding | 526/206 |
| 4,167,464 | 9/1979 | George | 526/240 |
| 4,248,736 | 2/1981 | Fuchigami et al. | 604/4 |
| 4,360,015 | 11/1982 | Mayer | 128/156 |
| 4,538,603 | 9/1985 | Pawelchak et al. | 128/156 |
| 4,793,337 | 12/1988 | Freeman et al. | 128/156 |

*Primary Examiner*—Alan Cannon
*Assistant Examiner*—Paul Prebilic
*Attorney, Agent, or Firm*—Wegner, Cantor, Mueller & Player

[57] ABSTRACT

Provided is a wound dressing able to absorb significant quantities of wound exudate emitted from an open wound. In one construction, it has the capability of allowing moisture contained in the exudate to be transpired out of the dressing, thereby lengthening the useful life of the dressing and minimizing macerations.

Also provided is a hydrophilic absorbent polymeric layer adhered directly to the wound area of a patient, providing a wound dressing to manage wound fluids, thereby minimizing skin maceration by rapidly absorbing wound exudate and permitting the transpiration of water vapor from the liquid thus-absorbed into the atmosphere, which comprises a laminate having a hydrophilic absorbent polymeric layer attached to said fabric layer, said hydrophilic absorbent polymeric layer having been applied by pouring a monomer solution onto said fabric layer and thereafter curing to yield the polymeric layer, said hydrophilic absorbent polymeric layer upon exposure to wound exudate being self-adherent to the wound area; a fabric layer is adjacent thereto; a pressure-sensitive adhesive to maintain contact between said highly skin conformable elastomeric film and the facing fabric layer.

36 Claims, 3 Drawing Sheets

WOUND DRESSING WITH HYDROPHILIC ABSORBENT LAYER

CROSS-REFERENCE TO COPENDING APPLICATIONS

This application is a continuation of Ser. No. 089,204, filed Aug. 25, 1987, which is a continuation-in-part of Ser. No. 899,575, filed Aug. 25, 1986 (now abandoned).

BACKGROUND OF THE INVENTION

The present invention relates to wound dressings, and pertains more particularly to wound dressings primarily for application over wounds which would be expected to exude substantial amounts of fluid during the normal healing process.

Exudation from many types of skin lesions is normal during the healing process. Included are such wounds as Stage II and Stage III ulcers, second and third degree burns, skin grafts and donor sites, deep derm abrasions and lacerations. Conventional bandages or wound dressings readily absorbed fluids, when used for such lesions, and soon become saturated with exudate seeping from the open wound, necessitating frequent bandage or dressing changes. The frequent changes cause irritation of the wound, discomfort to the patient and increased health care costs. A wound dressing which would have the capability of absorbing exudate as it appears at the surface of an open wound and the ability to transmit absorbed moisture at a desired rate through the dressing to the backing layer (sometimes herein referred to as the "distal surface" of the dressing, the surface furthest removed from the wound when the dressing is in place over the wound) where it can evaporate from the dressing would be particularly useful as a wound covering. Since such dressing could remain in place over the wound without needing to be changed for a longer period of time than conventional dressings, the wound would not be disturbed as frequently as a result of dressing changes and the patient would not experience as much discomfort from the associated trauma.

Various attempts have been made to provide a wound dressing that is capable of more effectively absorbing exudate seeping from an open wound.

In U.S. Pat. No. 3,339,546, a dressing comprised of a water-impervious film having an adhesive layer plied with the water-impervious film is described. The adhesive layer is disclosed as being a blend of a water-soluble or water-swellable hydrocolloid material dispersed throughout a water-insoluble viscous elastic binder.

U.S. Pat. No. 3,972,328 describes a wound dressing consisting of three components, namely, (1) a middle layer comprised of a semi-open cell flexible foam, (2) a water-impervious flexible film attached over one surface of the middle layer, and (3) a pressure-sensitive adhesive layer disposed over the other surface of the middle layer. The pressure-sensitive adhesive component is formed of a pressure-sensitive elastomer containing a water-soluble or water-swellable hydrocolloid or mixture of such hydrocolloids and contains, additionally, a tackifier and a plasticizer or solvent.

Although the use of water-soluble or water-swellable hydrocolloids dispersed in the adhesive layer of a wound dressing allows wound exudate to be absorbed by the hydrocolloids, the absorption of the exudate by the particles of hydrophilic material, with attendant swelling of the particles, prematurely destroys the integrity of the adhesive film resulting in the film's disintegration.

SUMMARY OF THE INVENTION

The present invention provides a wound dressing that is able to absorb significant quantities of wound exudate emitted from an open wound without the integrity of the dressing being destroyed and, in one preferred construction, has the capability of allowing moisture contained in the exudate to be transferred within a desired rate through the dressing to the distal surface of the dressing where it can evaporate into the surrounding atmosphere, thereby lengthening the useful life of the dressing. In accordance with the invention a wound dressing is provided that includes a fabric layer (sometimes hereinafter referred to as a layer of fabric) in which a flexible essentially continuous film of a hydrophilic material may be deposited, preferably which is a hydrophilic absorbent polymeric layer applied to or impregnated within the fabric layer. A layer of a pressure-sensitive adhesive material is adhered to one side of the fabric for affixing the dressing to the patient, the adhesive material being one that will adhere to the healthy skin of the patient, but tends not to adhere to the open wound itself. To provide additional integrity to the dressing, an exterior cover layer is provided that forms the distal surface of the dressing, i.e., the surface of the dressing furthest removed from the wound when the dressing is in place over the wound. In certain aspects of the present invention, component layers of the dressing preferably have a porosity such that moisture contained in the body fluid can pass through the dressing at a desired rate and be evaporated at the backing or distal face of the dressing.

A final aspect of the invention provides the hydrophilic absorbent polymeric layer adhered directly to the wound area of a patient. More particularly there is provided a wound dressing to manage wound fluids, thereby minimizing skin maceration by rapidly absorbing wound exudate and permitting the transpiration of water vapor from the liquid thus-absorbed into the atmosphere, which comprises a laminate having a hydrophilic absorbent polymeric layer attached to said fabric layer, said hydrophilic absorbent polymeric layer having been applied by pouring a monomer solution onto said fabric layer and thereafter curing to yield the polymeric layer, said hydrophilic absorbent polymeric layer upon exposure to wound exudate being self-adherent to the wound area; a fabric layer is adjacent thereto. Remote from the hydrophilic absorbent polymeric layer is a highly skin-conformable elastomeric bacterial barrier film to produce intimate skin contact with the wound area of a patient and to cover said wound dressing with a pressure-sensitive adhesive maintaining contact between the highly skin conformable elastomeric film and the facing fabric layer. Each of the layers has a moisture vapor transmission rate sufficient to permit transpiration of vapor from fluid absorbed in said wound dressing, whereby maceration of the neoendotheliazing wound bed and surrounding wound area is minimized.

DETAILED DESCRIPTION OF THE INVENTION

In accordance with a first aspect of the present invention, there is provided an occlusive wound dressing capable of retention of wound exudate which comprises a laminate having the following layers:
  (a) an adhesive layer capable of permitting passage of liquid therethrough, said adhesive layer upon pressure contact with the skin of a patient permitting prolonged adhesion of said wound dressing to said skin without necessity of any external securing means;
  (b) a fabric layer being bonded to said adhesive layer which retains structural integrity upon exposure of said wound dressing to said wound exudate;
  (c) a hydrophilic absorbent polymeric layer applied to said fabric layer, said hydrophilic absorbent polymeric layer having been applied to or impregnated within the fabric layer, the resultant fabric having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed on the wounded skin of a patient; and
  (d) at least one occlusive backing layer selected from a member consisting of a film, foam, foam-film laminate or fabric, said backing layer being attached to protruding fibers of the absorbent/fabric layer through a second adjacent adhesive layer.

The hydrophilic absorbent polymeric layer which is common to all aspects of the present invention may be made from a variety of polymers, and should be capable of absorbing 2 to 20 times its weight of exudate. Such hydrophilic materials include sodium carboxymethylcellulose, various polyacrylamide, polyacrylonitrile and acrylic acid polymers, Karaya gum and polysaccarides. As hydrophilic layer 15, a non-toxic flexible film formed of a cross-linked acrylic acid polymer prepared by photo- or radiation-polymerizing (in a nitrogen atmosphere) 90 to 99.9 weight percent of acrylic acid, 50 to 100% of the carboxylic groups having been neutralized with an alkali metal hydroxide or ammonium hydroxide prior to polymerization, with 0.1 to 10 percent of a polyfunctional cross-linking agent and 0.1 to 5 weight percent of a photo-initiator based on the total weight of acrylic acid and cross-linking agent, such polymers being more fully described in Canadian Patent No. 1,160,984 issued Jan. 24, 1984, has been found to be particular effective. Other useful hydrophilic materials are those described in U.S. Pat. Nos. 4,062,817 and 4,066,583. Useful polymers and a method for making such polymers is disclosed in commonly owned patent publication, U.S. Pat. No. 4,167,464, and European Patent Specification No. 0 042 406, published June 19, 1985. Acrylics and acrylates, which may be either unsubstituted or variously substituted, may be used, particularly in accordance with the literature references.

In accordance with a preferred embodiment of this aspect of the present invention wherein said hydrophilic absorbent is cured from a monomer solution applied to or impregnated within said fabric layer. In the preferred embodiment, the monomer solution may be either a solution of a single monomer, or a mixture of monomers, whereby a copolymer is produced upon curing of the cast monomer solution.

In accordance with a preferred embodiment of this aspect of the present invention said adhesive layer is a pharmaceutically acceptable porous pressure-sensitive acrylic adhesive. In accordance with a preferred embodiment of this aspect of the present invention said fabric layer is composed of a polyester selected from the group consisting of a polyester which is spun-bonded, spun-laced or point-bonded.

In one embodiment, said hydrophilic absorbent is a cross-linked acrylic. In accordance with a preferred embodiment of this aspect of the present invention the said hydrophilic absorbent polymer is an alginate or sodium carboxymethylcellulose.

In accordance with a preferred embodiment of the first aspect of the present invention there is provided an occlusive wound dressing capable of retention of wound exudate which comprises a laminate having the following layers:
  (a) an adhesive layer capable of permitting passage of liquid therethrough, said adhesive layer upon pressure contact with the skin of a patient permitting prolonged adhesion of said wound dressing to said skin without necessity of any external securing means;
  (b) a fabric layer having bonded to said adhesive layer which retains structural integrity upon exposure of said wound dressing to said wound exudate;
  (c) a hydrophilic absorbent polymeric layer attached to said fabric layer, said hydrophilic absorbent polymeric layer having been (i) applied to or impregnated within the fabric layer; and (ii) brushing the top surface of the resultant absorbent/fabric composite to yield a plurality of raised fibers; the thus-impregnated fabric having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed on the wounded skin of a patient;
  (d) an adhesive layer attached to the brushed composite wherein said protruding fibers are attached to the adjacent adhesive layer; and
  (e) at least one occlusive backing layer selected from a member consisting of a film, foam, foam-film laminate or fabric, said backing layer being attached to said protruding fibers through the adjacent adhesive layer.

In accordance with a second aspect of the present invention there is provided a wound dressing to manage wound fluids thereby minimizing skin maceration by rapidly absorbing wound exudate and permitting the transpiration of water vapor from the liquid thus-absorbed into the atmosphere, which comprises a laminate having the following layers:
  (a) an adhesive layer capable of permitting passage of liquid therethrough, said adhesive layer upon pressure contact with the skin of a patient permitting prolonged adhesion of said wound dressing to said skin without necessity of any external securing means;

(b) a fabric layer having bonded to said adhesive layer which retains structural integrity upon exposure of said wound dressing to said wound exudate;

(c) a hydrophilic absorbent polymeric layer attached to said fabric layer, said hydrophilic absorbent polymeric layer having been applied to or impregnated within the fabric layer, the resultant fabric having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed on the wounded skin of a patient; and (d) at least one backing layer selected from the group consisting of a film, foam, foam-film laminate or fabric, said backing layer being attached to protruding fibers of the absorbent/fabric layer through a second adjacent adhesive layer wherein each of the layers has a moisture vapor transmission rate sufficient to permit transpiration of vapor from fluid absorbed in said wound dressing, whereby maceration of the neoendotheliazing wound bed and surrounding wound area is minimized.

In accordance with a preferred embodiment of this aspect of the present invention said hydrophilic absorbent is cured from a monomer solution applied to or impregnated within said fabric layer. The same monomers as used in the first aspect of the present invention may be used in this aspect. In accordance with a preferred embodiment of this aspect of the present invention said adhesive layer is a pharmaceutically acceptable porous pressure-sensitive acrylic adhesive. In accordance with a preferred embodiment of this aspect of the present invention said fabric layer is composed of a polyester selected from the group consisting of a polyester which is spun-bonded, spun-laced or point-bonded. In accordance with a preferred embodiment of this aspect of the present invention the hydrophilic absorbent is a cross-linked acrylic. In another aspect, said hydrophilic absorbent polymer is an alginate or sodium carboxymethyl-cellulose. In this embodiment, the hydrophilic absorbent polymer is preferably dispersed in styrene-butadiene-styrene block copolymer.

In accordance with another embodiment of the second aspect of the present invention there is provided a wound dressing to manage wound fluids thereby minimizing skin maceration by rapidly absorbing wound exudate and permitting the transpiration of water vapor from the liquid thus-absorbed into the atmosphere, which comprises a laminate having the following layers:

(a) an adhesive layer capable of permitting passage of liquid therethrough, said adhesive layer upon pressure contact with the skin of a patient permitting prolonged adhesion of said wound dressing to said skin without necessity of any external securing means;

(b) a fabric layer having bonded to said adhesive layer which retains structural integrity upon exposure of said wound dressing to said wound exudate;

(c) a hydrophilic absorbent polymeric layer attached to said fabric layer, said hydrophilic absorbent polymeric layer having been applied to or impregnated within the fabric layer; and brushing the top surface of the resultant absorbent/fabric composite to yield a plurality of raised fibers; the thus-cured absorbent polymeric layer, the thus-impregnated fabric having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed on the wounded skin of a patient;

(d) an adhesive layer attached to the brushed composite absorbent polymeric layer, wherein said protruding fibers are attached to the adjacent adhesive layer;

(e) at least one backing layer selected from the group consisting of a film, foam, foam-film laminate or fabric, said backing layer being attached to said protruding fibers through the adjacent adhesive layer wherein each of the layers has a moisture vapor transmission rate sufficient to permit transpiration of vapor from fluid absorbed in said wound, dressing, whereby maceration of the neoendotheliazing wound bed and surrounding wound area is minimized.

The hydrophilic absorbent is cured from a monomer solution applied to or impregnated within said fabric layer, in accordance with a preferred embodiment of this aspect of the present invention. The same monomers as used in the first aspect of the present invention may be used in this aspect. In accordance with a preferred embodiment of this aspect of the present invention said adhesive layer is a pharmaceutically acceptable porous pressure-sensitive acrylic adhesive. In accordance with a preferred embodiment of this aspect of the present invention said fabric layer is composed of a polyester selected from the group consisting of a polyester which is spun-bonded, spun-laced or point-bonded. In accordance with a preferred embodiment of this aspect of the present invention the hydrophilic absorbent is a cross-linked acrylic. In another aspect, said hydrophilic absorbent polymer is an alginate or sodium carboxymethyl-cellulose. In this embodiment, the hydrophilic absorbent polymer is preferably dispersed in styrene-butadiene-styrene block copolymer.

In accordance with a third aspect of the present invention there is provided a wound dressing which comprises a laminate having the following layers:

(a) an adhesive layer capable of permitting passage of liquid therethrough, said adhesive layer upon pressure contact with the skin of a patient permitting prolonged adhesion of said wound dressing to said skin without necessity of any external securing means;

(b) a fabric layer being bonded to said adhesive layer which retains structural integrity upon exposure of said wound dressing to said wound exudate;

(c) a hydrophilic absorbent polymeric layer applied to said fabric layer, said hydrophilic absorbent polymeric layer having been applied to or impregnated within the fabric layer, the resultant fabric having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed on the wounded skin of a patient;

(d) at least one backing layer placed over said layer (c) absent a pressure-sensitive adhesive layer therebetween; and (e) a die-cut perimeter substrate layer with adhesive on both sides, to overlap the skin adhesive (a) on the first adhesive face and overlap to attach the backing layer (d) on a second adhesive face.

In one embodiment there is provided an occlusive wound dressing which is capable of retention of wound exudate wherein the backing layer (d) is occlusive, said exudate being maintained in an expanded layer (c) caused by absorption of exudate fluid from the wound. Alternatively, there is provided a wound dressing to manage wound fluids thereby minimizing skin maceration by rapidly absorbing wound exudate and permitting the transpiration of water vapor from the liquid thus-absorbed into the atmosphere, wherein each of the layers has a moisture vapor transmission rate sufficient to permit transpiration of vapor from fluid absorbed in said wound dressing, whereby maceration of the neoendotheliazing wound bed and surrounding wound area is minimized.

In either variation, in a preferred embodiment the hydrophilic absorbent is cured from a monomer solution applied to or impregnated within said fabric layer. In a preferred embodiment, said adhesive layer is a pharmaceutically acceptable porous pressure-sensitive acrylic adhesive. In another embodiment, the fabric layer is composed of a polyester selected from the group consisting of a polyester which is spun-bonded, spun-laced or point-bonded. The hydrophilic absorbent in a preferred embodiment is a cross-linked acrylic. In another embodiment, the hydrophilic absorbent is a polymer which is an alginate or hydrophilic absorbent polymeric layer is made from sodium carboxymethylcellulose.

In accordance with a final aspect of the present invention there is provided a wound dressing to manage wound fluids thereby minimizing skin maceration by rapidly absorbing wound exudate and permitting the transpiration of water vapor from the liquid thus-absorbed into the atmosphere, which comprises a laminate having the following layers:

(a) a highly skin-conformable elastomeric bacterial barrier film to produce intimate skin contact with the wound area of a patient and to cover said wound dressing;

(b) an pressure-sensitive adhesive to maintain contact between said highly skin conformable elastomeric film and the facing fabric layer;

(c) a fabric layer; and (d) a hydrophilic absorbent polymeric layer attached to said fabric layer, said hydrophilic absorbent polymeric layer having been applied by pouring a monomer solution onto said fabric layer and thereafter curing to yield the polymeric layer, said hydrophilic absorbent polymeric layer upon exposure to wound exudate being self-adherent to the wound area wherein each of the layers has a moisture vapor transmission rate sufficient to permit transpiration of vapor from fluid absorbed in said wound dressing, whereby maceration of the neoendotheliazing wound bed and surrounding wound area is minimized.

In this final aspect of the invention there is provided as said hydrophilic absorbent a cross-linked acrylic. The hydrophilic absorbent polymeric layer is made of the same polymer material as used in the other aspects of the invention. Also in this final aspect of the invention there is provided as said adhesive layer a pharmaceutically acceptable porous pressure-sensitive acrylic adhesive. The fabric layer may be composed of a polyester selected from the group consisting of a polyester which is spun-bonded, spun-laced or point-bonded.

Figure 1:
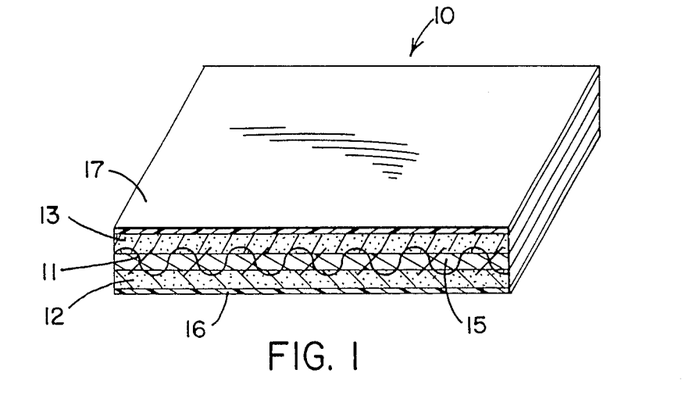
FIG. 1 is a perspective view of a segment of a wound dressing embodying one aspect of the present invention.

The drawings illustrate certain aspects of the present invention. The wound dressing 10, shown in FIG. 1, is comprised of a fabric layer 11 plied with and adhered to a layer 12 of an adhesive material over one of its broadside faces (its inward broadside face) and a second layer 13 of an adhesive material over its other broadside face (its distal broadside face). Adhesive layers 12 and 13 desirably are pressed into fibers protruding outwardly from the surfaces of the fabric layer 11 so that the adhesive becomes mechanically bonded with the fiber ends protruding from the body of fabric layer 11. A layer 15 of a flexible hydrophilic material is disposed between adhesive layers 12 and 13 and within fabric layer 11. A release layer 16 is disposed over and releasable secured to the exposed broadside surface of adhesive layer 12 to protect adhesive layer 12 during storage of dressing 10, layer 16 being removed just prior to the application of dressing 10 over the wound. A protective cover layer 17 is disposed exteriorly over fabric layer 11 and is bonded to fabric layer 11 by adhesive layer 13. Cover layer 17 not only serves as an outer protective layer providing a high degree of structural integrity to the dressing 10, but it also can function as a shield that prevents contaminants from gaining access to the interior of the dressing and, ultimately, to the wound.

Fabric layer 11 desirably is a flexible high-lofted, non-toxic fabric that has sufficient structural integrity to withstand normal handling, processing and use. Fabric layer 11 can be formed of any non-toxic fibers, such as cotton, nylon, rayon, polyester, and polyester cellulose fibers, and, if a non-woven fabric, it desirably is of a spun-bonded or spun-laced construction, although wet-laid or air-laid structures can be employed. The fabric desirably has numerous fibers protruding from its broadside faces to facilitate a secure mechanical bond between fabric layer 11 and adhesive layers 12 and 13. An example of a fabric that has been found to perform exceptionally well in wound dressings of the present invention are 4 to 14 mil thick spun-bonded polyester staple fiber fabrics sold by E. I. duPont de Nemours & Company under the trade designation "Reemay."

Adhesive layer 12 may be formed of any pressure-sensitive, not-toxic, adhesive suitable for adhesion to healthy normal human skin, although adhesive layer 12 will adhere to normal healthy skin, the adhesive has little, if any, tendency to adhere to the open wound itself and, therefore, minimizes any potential interference with normal healing, and minimizes trauma to the neoepithelium on removal of the dressing. In addition to being non-toxic, adhesive layer 12 desirably should be sterilizable by any conventional means (such as radiation, thermal or steam processes, although sterilization by gamma ray or electron beam irradiation is preferred), non-cytotoxic, non-sensitizing and have a appropriate moisture vapor transmission rate (MVTR) of at least 200 grams of water, preferably between 300 to 800 grams of water, per square meter per 24 hours at 50% relative humidity at 36° C. when measured in accordance with ASTM Procedure No. E96-80. Suitable pressure-sensitive skin adhesive compositions are pressure-sensitive polyacrylic skin adhesives (such as are available from Daubert Coated Products Company, and Fasson Division of Avery International Corporation, and Semex Medical of Seton Company), pressure-sensitive polyvinyl ether adhesives, and pressure-sensitive polyurethane adhesives.

Adhesive layer 13 may be formed of the same adhesive composition as adhesive layer 12 or it may be formed of a different adhesive composition provided that it is sterilizable by conventional processes and desirable has an MVTR of at least 200 grams of water, but preferably between 300 to 800 grams of water, per square meter per 24 hours at 50% relative humidity at 36° C. when measured in accordance with ASTM Procedure No. E96-80.

The flexible layer 15 of hydrophilic material disposed within fabric layer 11 and between adhesive layers 12 and 13 may be any flexible non-toxic hydrophilic material that is capable of retaining its integrity even after absorbing 2 to 20 times its weight of exudate. Such hydrophilic materials include sodium carboxymethylcellulose, various polyacrylamide, polyacrylonitrile and acrylic acid polymers, Karaya gum and polysaccharides. A non-toxic flexible film layer 15 formed of a cross-linked acrylic acid polymer prepared by photo- or radiation-polymerizing (in a nitrogen atmosphere) 90 to 99.9 weight percent of acrylic acid, 50 to 100% of the carboxylic groups having been neutralized with an alkali metal hydroxide or ammonium hydroxide prior to polymerization, with 0.1 to 10 percent of a polyfunctional cross-linking agent and 0.1 to 5 weight percent of a photo-initiator based on the total weight of acrylic acid and cross-linking agent, such polymers being more fully described in Canadian Patent No. 1,160,984 issued Jan. 24, 1984, has been found to be particular effective. Other useful hydrophilic materials are those described in U.S. Pat. Nos. 4,062,817 and 4,066,583. Useful polymers and a method for making such polymers is disclosed in commonly owned patent publication, U.S. Pat. No. 4,167,464, and European Patent Specification No. 0 042 406, published June 19, 1985. Acrylics and acrylates, which may be either unsubstituted or variously substituted, may be used, particularly in accordance with the literature references.

Cover layer 17 may be formed of any non-toxic material that is sterilizable by conventional processes and desirably has an MVTR of at least 200 grams of water, preferably between 300 to 800 grams of water, per square meter per 24 hours at 50% relative humidity at 36° C. when measured in accordance with ASTM Procedure No. E96-80. Desirably, cover layer 17 is from 0.5 to 2.0 mils thick and typically may be polyester polyurethane, a polyether polyurethane, polyethylene, copolyester, or polyether block imide film.

To provide dressing 20 with the ability to transmit moisture through the dressing 10 and an MVTR of between 300 to 800 grams of water, per square meter per 24 hours at 50% relative humidity at 36° C. when measured in accordance with ASTM Procedure No. E96-80, it is necessary that all component layers of dressing 10 have an MVTR of at least 300 grams of water per square meter per 24 hours at 50% relative humidity at 36° C. and that at least one of the layers, and preferably cover layer 17, have an MVTR of between 300 to 800 grams of water per square meter per 24 hours at 50% relative humidity at 36° C. when measured in accordance with ASTM Procedure No. E96-80.

An alternative wound dressing exudate management system contemplated by the present invention is an occlusive wound dressing capable of retention of wound exudate fluids. In this embodiment, at least one layer, preferably cover layer 17, has a low MVTR. In this design, the fluid remains adsorbed within the fabric/hydrogel composite of the wound dressing.

Figure 2:
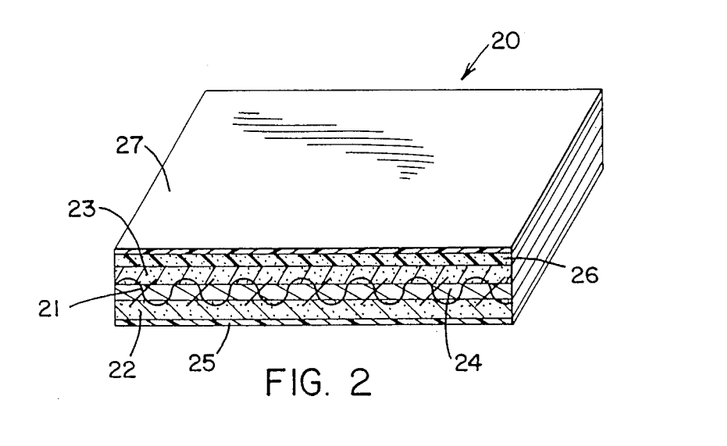
FIG. 2 is a perspective view of a segment of another aspect of the present invention.

Wound dressing 20, shown if FIG. 2, is comprised of a fabric layer 21 with a layer 22 of a pressure-sensitive adhesive material over one of its broadside faces and a second layer 23 of an adhesive material over its other broadside face. Like adhesive layers 12 and 13 of dressing 10, adhesive layers 22 and 23 of dressing 20 desirably are pressed into fibers protruding outwardly from the respective broadside faces of fabric layer 21 with which they are associated to promote mechanical bonds between adhesive layers 22 and 23 and fabric layer 21. A layer 24 of a flexible hydrophilic material is disposed between adhesive layers 22 and 23 within fabric layer 21. A releasable protective layer 25 is disposed over the exposed broadside face of adhesive layer 22 to protect adhesive layer 22 during storage, layer 25 being removed immediately before dressing 20 is placed over the wound. A layer 26 of an open-cell sponge material is adhered to the exterior broadside face of adhesive layer 23. Sponge layer 26 provides a degree of cushioning protection to a wound against forces externally applied against dressing 20 when dressing 20 is in place over a wound. An optional cover layer 27 is disposed over and adhered to layer 26 and not only can serve to impart structural integrity to dressing 20, but also can serve as a shield that prevents contaminants from gaining access to the interior of dressing 20. Layers 21, 22, 23, 43, 25 and 27 of dressing 20 correspond functionally to layers 11, 12, 13, 15 and 17, respectively, of dressing 10, and may be formed of the same materials as described in regard to their respective counterparts of dressing 10.

Sponge layer 26 may be made of any flexible, open-cell cellular material that has sufficient integrity to withstand clinical handling, is sterilizable by conventional processes, and desirably has an MVTR of at least 200 grams of water per square meter per 24 hours at 50% relative humidity at 36° C. when measured in accordance with ASTM Procedure No. E96-80. Layer 26 may be from about 1 to 25 mm thick, but preferably is from about 1 to 3 mm thick. Latex foam rubber, polyvinyl chloride foam, polyethylene foam and polyurethane foam materials which have from 40 to 100 pores per linear inch (PPI) are typical cellular materials which can be used for fashioning sponge layer 26. If sponge layer 26 has an exterior skin layer, such skin layer can serve in place of cover layer 27. An 80 PPI open-cell polyurethane foam sold by General Foam Plastics Corporation or Scotfoam Co. of General Felt Industry Corporation is particularly useful for forming sponge layer 26. Layer 26 can be bonded or adhered to cover layer 27 by any suitable convenient manner such as by flame bonding, thermal bonding or through use of an adhesive layer (not shown) that can be the same adhesive material as used in adhesive layers 22 and 23 or any other compatible bonding system.

If dressing 20 is to have the capability of transmitting moisture at a rate of from 300 to 800 grams of water per square meter per 24 hours at 50% relative humidity at 36° C. when measured in accordance with ASTM Procedure No. E96-80, all of the component layers of dressing 20 must have an MVTR of at least 300 grams of water per square meter per 24 hours at 50% relative humidity at 36° C. and at least one of the layers, preferably cover layer 27, must have an MVTR of between 300 to 800 grams of water per square meter per 24 hours at 50% relative humidity at 36° C. when measured in accordance with ASTM Procedure No. E96-80.

An occlusive design having at least one layer of the dressing with a low MVTR is also contemplated in dressings having a foam or foam/film cover layer.

In the manufacture of dressing 10, a continuous sheet of a composite "A" may be formed by combining continuous sheets of fabric layer 11, adhesive layer 12 and release layer 16 together in any convenient manner. For example, a continuous sheet of adhesive layer 12 supported on release layer 16 can be applied onto one broadside face of a continuous sheet of fabric layer 11. The three components then can be passed between pressure rolls (not shown) to force fibers protruding from the broadside face of fabric layer 11 opposing adhesive layer 12 into adhesive layer 12 to form a firm mechanical bond between fabric layer 11 and adhesive layer 12. The continuous sheet of composite "A" then can be wound on a roll 30 for storage and later use.

Figure 3:
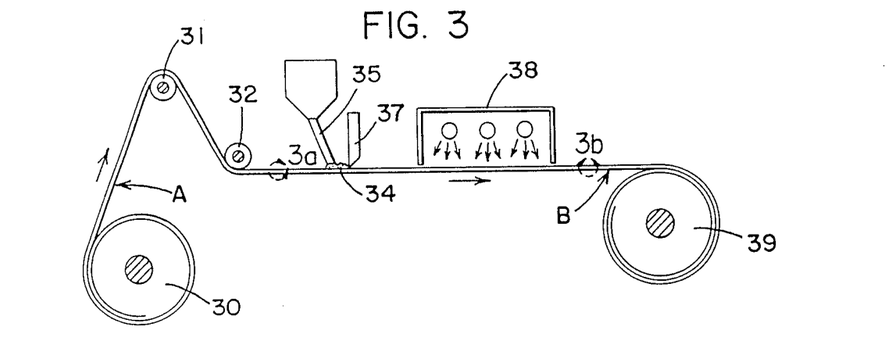
FIGS. 3, 3a, 3b is a schematic view illustrating forming a composite component of the wound dressings of FIGS. 1 and 2.
Figure 3A:
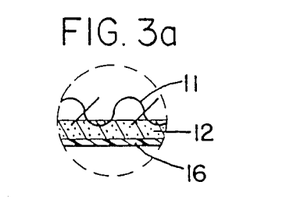
Figure 3B:
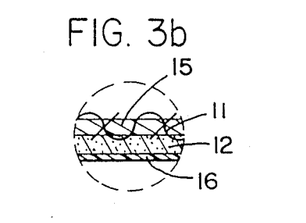

As schematically shown in FIG. 3, the layer of hydrophilic material can be formed within fabric layer 11 by unwinding the sheet of composite A from roll 30, passing the sheet of composite A over tensioning rolls 31 and 32 and advancing the sheet of composite A with the fabric layer 11 facing up beneath a spray or bank 34 of hydrophilic film-producing material emitted by nozzle 35. Composite A with the hydrophilic film-producing material deposited thereon then passes beneath doctor blade 37. Doctor blade 37 forces the hydrophilic film-producing material into the central region of fabric layer 11 and controls the thickness of the resultant hydrophilic film (15). The composite then is passed through a drying oven or a polymerization chamber 38 depending upon whether the hydrophilic film-producing material used merely needs to be dried or whether it needs to be polymerized. If the hydrophilic film-producing material is one that requires polymerization such as those described in Canadian Patent No. 1,160,984, polymerization chamber 38 may contain sources of electron beams or ultraviolet (UV) light energy to cause the hydrophilic film-producing material to polymerize. The resulting continuous sheet of composite "B" consisting of fabric layer 11, hydrophilic film layer 15 deposited within fabric layer 11, adhesive layer 12 and release layer 16 then can be wound upon a roll 39 for storage.

A continuous sheet of a composite "C" consisting of adhesive layer 13 and cover layer 17 may be formed by combining continuous sheets of adhesive layer 13 and cover layer 17 in any convenient manner. For example, a continuous sheet of adhesive layer 13 can be applied over cover layer 17. Then the two layers can be passed between pressure rolls (not shown) to form the composite. The continuous sheet of composite C then can be wound on a roll 40 for storage and later use.

Figure 4:
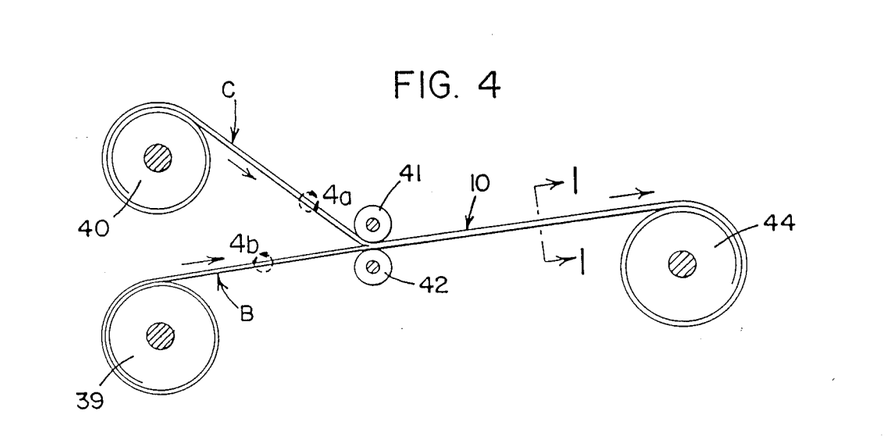
FIGS. 4, 4a, 4b is a schematic view illustrating combining together two composite components to form the wound dressing shown in FIG. 1.
Figure 4A:
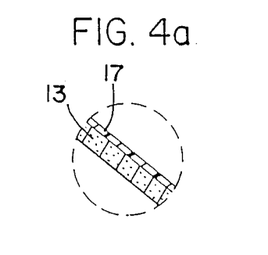
Figure 4B:
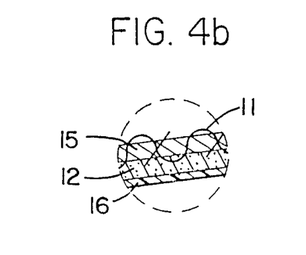

The sheets of composite B and composite C then can be combined with adhesive layer 13 of composite C in facing relationship with fabric layer 11 of composite B, as schematically shown in FIG. 4. The combined sheets of composite B and composite C then are passed between pressure rolls 41, 42 to cause the protruding fibers of fabric layer 11 to be pressed into adhesive layer 13 to form a mechanical bond between fabric layer 11 and adhesive layer 13 thereby completing the manufacture of wound dressing 10 except for cutting and packaging the composite sheet in dressings of desired size. In the interim, the continuous sheet of dressing 10 can be wound on roll 44. Of course, if desired, the process of making wound dressing 10 can be a continuous type of operation.

Alternatively, an adhesive layer may be laminated on the sheets of composite B to form a modified composite $B^1$. Then composite $B^1$ having its adhesive face up is passed through pressure rolls along with a sheet of cover layer 17 to form the completed dressing.

During this process, it may be necessary to brush the top (fabric/hydrogel) surface of composite B prior to lamination of the adhesive to insure that sufficient numbers of protruding fibers are present to allow a strong bond to form between the adhesive layer and fabric layer. This is important for the structural integrity of the modified composite $B^1$.

Figure 5:
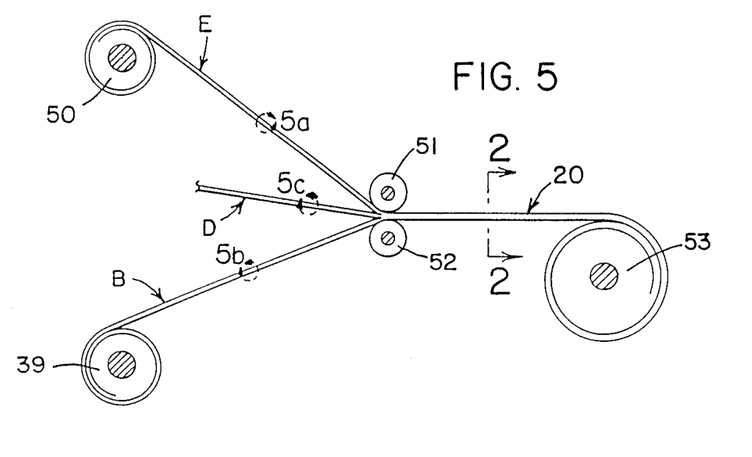
FIG. 5, 5a, 5b, 5c is a schematic view illustrating combining together two composite components with an adhesive layer to form the wound dressing of FIG. 2.
Figure 5A:
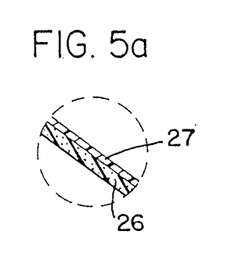
Figure 5B:
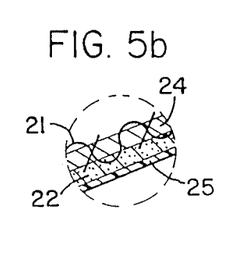
Figure 5C:
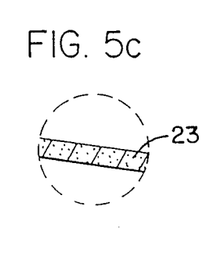

Wound dressing 20 may be manufactured, as schematically illustrated in FIG. 5. A continuous sheet of composite B (as described above) wound on roll 39 is plied with a continuous sheet of adhesive "D" which is a sheet of the adhesive material that forms adhesive layer 23 of dressing 20, and a continuous sheet of composite "E" wound on roll 50. Composite E consists of sponge layer 26 optionally bonded to cover layer 27 either by flame bonding, thermal bonding or by a layer of adhesive material (not shown). In combining composites B and E with adhesive layer D, the exposed face of fabric layer 21 is brought in contact with one face of adhesive sheet D while the exposed face of sponge layer 26 is brought in contact with the opposite face of adhesive sheet D. The assembly then is passed between the nip of pressure rolls 52, 52 which causes adhesive sheet D to bond both to sponge layer 26 and to fabric layer 21 to form the dressing 20. The completed dressing 20 can be wound onto roll 53 to await being cut into convenient sizes and packaged. Again, the various steps of assembling dressing 20 can be performed as a continuous operation.

Alternatively, the adhesive layer D can be adhered to composite B to form a modified composite $B^1$ prior to lamination of the foam or foam/film "composite" E. The modified composite $B^1$ having its adhesive face up is then Passed through pressure rolls along with the composite E to form the completed dressing.

During this process, it may be necessary to brush the top (fabric/hydrogel) surface of composite B prior to lamination of the adhesive to insure that sufficient numbers of protruding fibers are present to allow a strong bond to form between the adhesive layer and fabric layer. This is important for the structural integrity of the modified composite $B^1$.

Desirably, the wound dressings have oxygen permeability when wetted by wound exudate to provide transmission of at least 2000, preferably 5000, cc of oxygen per square meter per 24 hours at 25° C. and relative humidity between 20 to 55%, when measured in accordance with ASTM Procedure No. D3985-81.

This application incorporates into the disclosure of U.S. Pat. No. 4,167,464, and European Patent Specification No. 0 042 406, published June 19, 1985.

The following examples illustrate the invention:

EXAMPLE I

A combined adhesive-fabric layer is used as a substrate, which has the following characteristics:

MDO 129 (Semex), a porous polyacrylate adhesive, is laminated on Reemay 2214 (Reemay, Inc.) to form a composite A sodium acrylate/acrylic acid monomeric emulsion is applied to the fabric side of this composite, and cured by UV radiation to yield a layer having a thickness of 0.075 mm and a coating weight of 1.2 g/ft2. The thickness and coating weight parameters of the wound dressing of the present invention are preferably between about 0.01 and about 0.50 mm and between about 1.0 and about 5.0 g/ft2. respectively. The resultant fabric has structural integrity to remain bonded to said adhesive layer when the wound dressing is exposed to the wound exudate, and the polymer is capable of absorbing the liquid drawn into said wound dressing from said wound exudate when said wound dressing is placed on the wounded skin of a patient.

EXAMPLE II

Onto the polymer side of the product of Example I there is affixed a high moisture vapor transmission rate polyacrylate adhesive, I-780 (Avery) and onto that adhesive there is adhered an occlusive film of polyethylene which does not permit passage of the liquid into the atmosphere.

EXAMPLES III-VII

The procedure of Example II may be followed, but instead of the film there may be substituted the following materials:

| | |
|---|---|
| Film | Polyvinylchloride |
| Foam | Polyvinylchloride foam |
| Foam-film | Polyvinylchloride foam with a polyethylene cover film |
| Foam | Polyethylene foam |
| Film | Polyvinylidene dichloride. |

EXAMPLE VIII

The procedure of Example I is followed, except that after the curing of the polymer layer, the thus-cured polymer is brushed so that there are protrusions of polymer sticking up from the surface.

EXAMPLES IX-XIII

Instead of attaching the occlusive backing layer to the product of Example I, the procedure of Examples III-VII is followed using instead the brushed polymer substrate produced in Example VI. Greater structural integrity is obtained due to the protrusions of the brushed fabric.

EXAMPLE XIV

A combined adhesive-fabric layer is used as a substrate, which has the following characteristics:

MDO 129 (Semex) is laminated to Reemay 2415 spun-bonded polyester (Reemay, Inc.). This composite is available as CM 5383-02 (Semex).

A calcium alginate film is coated over the fabric side of the composite to yield a layer having a thickness of 0.2 mm and a coating weight of 3 g/ft2.

EXAMPLE XV

Instead of the alginate of Example XIV, there is substituted sodium carboxymethylcellulose dispersed in Shell's Kraton SBS #G160 to yield a comparable product.

EXAMPLES XVI-XIX

In Examples I and VIII, XIV and XV, the polymer-coated fabric without the occlusive backing layer has the capacity to be formed into a wound dressing to manage wound fluids thereby minimizing skin maceration by rapidly absorbing wound exudate and permitting the transpiration of water vapor from the liquid thus-absorbed into the atmosphere.

Characteristic of this aspect of the invention the backing layer is a film, foam, foam-film laminate or fabric which has a moisture vapor transmission rate sufficient to permit transpiration of the vapor from fluid absorbed in said wound dressing, whereby maceration of the neoendotheliazing wound bed and surrounding wound area is minimized.

Thus, a backing layer of reticulated polyurethane foam with: polyurethane film or polyether blockimide or polyester high moisture vapor transmission rate films attached is laminated onto the aforementioned composite.

EXAMPLE XX

A combined adhesive-fabric layer is used as a substrate, which has the following characteristics:

MDO 129 (Semex), a porous polyacrylate adhesive, is laminated on Reemay 2214 (Reemay, Inc.) to form a composite. This composite is available as CM 5383-02 (Semex).

Polysulfonamide is applied to the fabric side of this composite, and cured by UV radiation to yield a layer having a thickness of 0.5 mm and a coating weight of 5 g/ft2. The resultant fabric has structural integrity to remain bonded to said adhesive layer when the dressing is exposed to the wound exudate, and the polymer is capable of absorbing the liquid drawn into said wound dressing from said wound exudate when said wound dressing is placed on the wounded skin of a patient.

EXAMPLE XXI

A wound dressing to manage wound fluids thereby minimizing skin maceration by rapidly absorbing wound exudate and permitting the transpiration of water vapor from the liquid thus-absorbed into the atmosphere. Laid directly onto the polymer side of the product of Example I without an adhesive is a backing layer which permits passage of the liquid into the atmosphere. A die-cut perimeter substrate layer having adhesive on both sides, 1522 double-faced polyethylene tape (3M) overlaps the skin adhesive of the product of Example I and also overlaps to attach the backing layer on said second face. An enhanced transpiration rate is achieved.

EXAMPLE XXII-XXIII

Example XXI is repeated using a polyester film and roticulated polyurethane foam, respectively as the backing layer.

EXAMPLE XXIV

This example illustrates a wound dressing to manage wound fluids thereby minimizing skin maceration by rapidly absorbing wound exudate and permitting the transpiration of water vapor from the liquid thus-absorbed into the atmosphere. Such a wound dressing includes
a highly skin-conformable elastomeric bacterial barrier film, a polyurethane film;

a pressure-sensitive adhesive between the barrier layer and the fabric, MDO 129 (Semex);

a fabric layer of Reemay spun-bond polyester; and a hydrophilic absorbent polymeric layer attached to the fabric layer, a poly(sodium acrylate).

The resultant product a moisture vapor transmission rate sufficient to permit transpiration of vapor from fluid absorbed in said wound dressing, whereby maceration of the neoendotheliazialing wound bed and surrounding wound area is minimized.

EXAMPLE XXV

Calcium alginate is substituted for the poly(sodium acrylate) of Example XXVI to yield comparable results.

EXAMPLE XXVI

Carboxymethylcellulose dispersed in styrene-butadiene-styrene is substituted for the poly(sodium acrylate) of Example XXIV to yield a comparable product.

EXAMPLE XXVII–XXIX

A polyether blockimide film is substituted for the Polyurethane film backing layer of Examples XXIV–XXVI to yield comparable products.

EXAMPLE XXX

Pharmaceuticals for topical release to a patient may be included in the wound dressings. For example, the medicament chlorhexidine may be dispersed in the polymeric layer and, as a result, be available to diffuse into the wound area upon use of the wound dressing.

What is claimed is:

1. An occlusive wound dressing capable of retention of wound exudate which comprises a laminate having the following layers:
   (a) an adhesive layer capable of permitting passage of liquid therethrough, said adhesive layer upon pressure contact with the skin of a patient permitting prolonged adhesion of said wound dressing to said skin without adhering to the wound;
   (b) a fabric layer having a fabric and protruding fibers being bonded to said adhesive layer which retains structural integrity upon exposure of said wound dressing to said wound exudate;
   (c) a hydrophilic absorbent polymeric layer comprising hydrophilic absorbent polymeric material which is deposited substantially within the fabric, said hydrophilic absorbent polymeric layer being impregnated substantially within the fabric, the resultant fabric having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed over the wound of a patient; and
   (d) at least one occlusive backing layer selected from the group consisting of a film, foam, foam-like laminate and fabric, said backing layer being attached to protruding fibers of said fabric through a second adjacent adhesive layer.

2. A wound dressing of claim 1, wherein said hydrophilic absorbent is an acylic and cured from a monomer solution applied to or impregnated within said fabric layer.

3. A wound dressing of claim 1, wherein said adhesive layer is a pharmaceutically acceptable porous pressure-sensitive acrylic adhesive.

4. A wound dressing of claim 1, wherein said fabric layer is composed of a polyester selected from the group consisting of a polyester which is spun-bonded, spun-laced or point-bonded.

5. A wound dressing of claim 2, in said hydrophilic absorbent is a cross-linked acrylic.

6. A wound dressing of claim 1, wherein said hydrophilic absorbent polymer is an alginate or sodium carboxymethylcellulose.

7. An occlusive wound dressing capable of retention of wound exudate which comprises a laminate having the following layers;
   (a) an adhesive layer capable of permitting passage of liquid therethrough, said adhesive layer upon pressure contact with the skin of a patient permitting prolonged adhesion of said wound dressing to said skin without adhering to the wound;
   (b) a fabric layer a fabric a fabric and having protruding fibers being bonded to said adhesive layer which retains structural integrity upon exposure of said wound dressing to said wound exudate;
   (c) a hydrophilic absorbent polymeric layer attached to said fabric layer, said hydrophilic absorbent polymeric layer comprising hydrophilic absorbent polymeric material which is deposited substantially within the fabric; the top surface of the resultant absorbent/fabric composite having a plurality of raised fibers resulting from brushing said top surface; the thus absorbent/fabric having structural integrity to remain bonded to said adhesive layer upon exposure of said wound dressing to said wound exudate, said hydrophilic absorbent polymer wound dressing from said wound exudate when said wound dressing is placed over the wound of a patient;
   (d) an adhesive layer attached to the brushed composite wherein said raised fibers (c) are attached to an adjacent adhesive layer; and
   (e) at least one occlusive backing layer selected from the group consisting of a film, foam, foam-like laminate and fabric, said backing layer being attached to said raised fibers through the adjacent adhesive layer (d).

8. A wound dressing of claim 7, wherein said hydrophilic absorbent is an acrylic and cured from a monomer solution applied to or impregnated within said fabric layer.

9. A wound dressing of claim 7, wherein said adhesive layer is a pharmaceutically acceptable porous pressure sensitive acrylic adhesive.

10. A wound dressing of claim 7, wherein said fabric layer is composed of a polyester selected from the group consisting of a polyester which is spun-bonded, spun-laced or point-bonded.

11. A wound dressing of claim 8, in said hydrophilic absorbent is a cross-linked acrylic.

12. A wound dressing of claim 7, wherein said hydrophilic absorbent polymer is an alginate or sodium carboxymethylcellulose.

13. A wound dressing to manage wound fluids thereby minimizing skin maceration by rapidly absorbing wound exudate and permitting the transpiration of water vapor from the liquid thus-absorbed into the atmosphere, which comprises a laminate having the following layers:
   (a) an adhesive layer capable of permitting passage of liquid therethrough, said adhesive layer upon pressure contact with the skin of a patient permitting prolonged adhesion of said wound dressing to said skin without adhering to the wound;

(b) a fabric layer having a fabric and protruding fibers being bonded to said adhesive layer which retains structural integrity upon exposure of said wound dressing to said wound exudate;

(c) a hydrophilic absorbent polymeric layer attached to said fabric layer, said hydrophilic absorbent polymeric layer comprising hydrophilic absorbent polymeric material which is deposited substantially within the fabric, the resultant fabric having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed over the wound of a patient; and (d) at least one backing layer selected from the group consisting of a film, foam, foam-like laminate or fabric, said backing layer being attached to a second adjacent adhesive layer, (e) each of the said layers has a moisture vapor transmission rate sufficient to permit transpiration of vapor from fluid absorbed in said wound dressing, whereby maceration of the neoendothelializing wound bed and surrounding wound area is minimized.

14. A wound dressing of claim 13, wherein said hydrophilic absorbent is an acrylic and cured from a monomer solution applied to or impregnated within said fabric layer.

15. A wound dressing of claim 13, wherein said adhesive layer is a pharmaceutically acceptable porous pressure-sensitive acrylic adhesive.

16. A wound dressing of claim 13, wherein said fabric layer is composed of a polyester selected from the group consisting of a polyester which is spun-bonded, spun-laced or point-bonded.

17. A wound dressing of claim 14, in said hydrophilic absorbent is a cross-linked acrylic.

18. A wound dressing of claim 13, wherein said hydrophilic absorbent polymer is an alginate or sodium carboxymethylcellulose.

19. A wound dressing to manage wound fluids thereby minimizing skin maceration by rapidly absorbing wound exudate and permitting the transpiration of water vapor from the liquid thus absorbed into the atmosphere, which comprises a laminate having the following layers:

(a) an adhesive layer capable of permitting passage of liquid therethrough, said adhesive layer upon pressure contact with the skin of a patient permitting prolonged adhesion of said wound dressing to said skin without adhering to the wound;

(b) a fabric layer having a fabric and protruding fibers being bonded to said adhesive layer which retains structural integrity upon exposure of said wound dressing to said wound exudate;

(c) a hydrophilic absorbent polymeric layer attached to said fabric layer, said hydrophilic absorbent polymeric layer comprising hydrophilic absorbent polymeric material which is deposited substantially within the fabric; the top surface of the resultant absorbent/fabric composite having a plurality of raised fibers resulting from brushing said top surface; the thus absorbent/fabric having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed over the wound of a patient;

(d) an adhesive layer attached to the brushed composite absorbent polymeric layer, wherein said raised fibers (c) are attached to an adjacent adhesive layer;

(e) at least one backing layer selected from the group consisting of a film, foam, foam-like laminate or fabric, said backing layer being attached to the adjacent adhesive layer (d)

(f) each of the said layers has a moisture vapor transmission rate sufficient to permit transpiration of vapor from fluid absorbed in said wound dressing, whereby maceration of the neoendothelializing wound bed and surrounding wound area is minimized.

20. A wound dressing of claim 19, wherein said hydrophilic absorbent is an acrylic and cured from a monomer solution applied to or impregnated within said fabric layer.

21. A wound dressing of claim 19, wherein said adhesive layer is a pharmaceutically acceptable porous pressure-sensitive acrylic adhesive.

22. A wound dressing of claim 19, wherein said fabric layer is composed of a polyester selected from the group consisting of a polyester which is spun-bonded, spun-laced or point-bonded.

23. A wound dressing of claim 20, in said hydrophilic absorbent is a cross-linked acrylic.

24. A wound dressing of claim 19, wherein said hydrophilic absorbent is polymer is an alginate or sodium carboxymethylcellulose.

25. A wound dressing which comprises a laminate having the following layers:

(a) an adhesive layer capable of permitting passage of liquid therethrough, said adhesive layer upon pressure contact with the skin of a patient permitting prolonged adhesion of said wound dressing to said skin without adhering to the wound;

(b) a fabric layer having a fabric and protruding fibers being bonded to said adhesive layer which retains structural integrity upon exposure of said wound dressing to said wound exudate;

(c) a hydrophilic absorbent polymeric layer comprising hydrophilic absorbent material which is deposited substantially within the fabric, said hydrophilic absorbent polymeric layer being impregnated substantially within the fabric, the resultant fabric layer having structural integrity to remain bonded to said adhesive layer upon exposure of said wound dressing to said wound exudate, said hydrophilic absorbent polymer layer capable of absorbing the liquid drawn into said wound dressing from said wound exudate when said wound dressing is placed over the wound of a patient;

(d) at least one backing layer placed over said hydrophilic absorbent polymeric layer (c) absent and additional pressure-sensitive adhesive layer therebetween; and (e) a die-cut perimeter substrate layer with adhesive on both sides having a first and second adhesive face, whereto overlap the adhesive layer (a) on the second adhesive face and overlap to attach the backing layer (d) on the second adhesive face.

26. A wound dressing of claim 25 to manage wound fluids thereby minimizing skin maceration by rapidly absorbing wound exudate and permitting the transpiration of water vapor from the liquid thus-absorbed into the atmosphere, wherein each of the layers has a moisture vapor transmission rate sufficient to permit transpiration of vapor from fluid absorbed in said wound dressing, whereby maceration of the neoendotheliazialing wound bed and surrounding wound area is minimized.

27. A wound dressing of claim 26, wherein said hydrophilic absorbent is an acrylic and cured from a monomer solution applied to or impregnated within said fabric layer.

28. A wound dressing of claim 26, wherein said adhesive layer is a pharmaceutically acceptable porous pressure-sensitive acrylic adhesive.

29. A wound dressing of claim 26, wherein said fabric layer is composed of a polyester selected from the group consisting of a polyester which is spun-bonded, spun-laced or point-bonded.

30. A wound dressing of claim 28, in said hydrophilic absorbent is a cross-linked acrylic.

31. A wound dressing of claim 26, wherein said hydrophilic absorbent is a polymer which is an alginate or hydrophilic absorbent polymeric layer made from sodium carboxymethylcellulose.

32. An occlusive wound dressing of claim 25 capable of retention of wound exudate wherein the backing layer (d) is occlusive, said exudate being maintained in layer (c) that expands when exudate fluid from the wound is absorbed.

33. A wound dressing to manage wound fluids thereby minimizing skin maceration by rapidly absorbing wound exudate and permitting the transpiration of water vapor from the liquid thus-absorbed into the atmosphere, which comprises a laminate having the following layers:
 (a) a highly skin-conformable elastomeric bacterial barrier film to produce intimate skin contact with the wound area of a patient and to cover said wound dressing;
 (b) a pressure sensitive adhesive layer applied on one side of said elastomeric film;
 (c) a fabric layer having a fabric and protruding fabrics; and
 (d) a hydrophilic absorbent polymeric layer attached to said fabric layer, said hydrophilic absorbent polymeric layer comprising hydrophilic absorbent material which is deposited substantially within the fabric having been applied by pouring a monomer solution onto said fabric layer and thereafter curing to yield the polymeric layer, said hydrophilic absorbent polymeric layer upon exposure to wound exudate being self-adherent to the wound area
wherein each of the layers has a moisture vapor transmission rate sufficient to permit transpiration of vapor from fluid absorbed in said wound dressing, whereby maceration of the neoendotheliazing wound bed and surrounding wound area is minimized.

34. A wound dressing of claim 33, in said hydrophilic absorbent is a cross-linked acrylic.

35. A wound dressing of claim 33, wherein said adhesive layer is a pharmaceutically acceptable porous pressure-sensitive acrylic adhesive.

36. A wound dressing of claim 33, wherein said fabric layer is composed of a polyester selected from the group consisting of a polyester which is spun-bonded, spun-laced or point-bonded.

* * * * *

UNITED STATES PATENT AND TRADEMARK OFFICE
CERTIFICATE OF CORRECTION

PATENT NO. : 4,977,892

DATED : December 18, 1990

INVENTOR(S) : Ralph X. Ewall

It is certified that error appears in the above-identified patent and that said Letters Patent is hereby corrected as shown below:

Column 9, lines 8 and 9, "desirable" should read ---desirably---.

Column 12, line 43, "Passed" should begin with a small "p".

Column 14, line 57, "roticulated" should read ---reticulated---.

Column 15, line 63, "acylic" should read ---acrylic---.

Column 16, line 55, "in" should read ---wherein---.

Column 17, line 40, "in" should read ---wherein---.

Column 18, line 32, "in" should read ---wherein---.

Column 19, line 21, "in" should read ---wherein---.

Column 20, line 26, "in" should read ---wherein---.

Signed and Sealed this

Eighth Day of September, 1992

Attest:

DOUGLAS B. COMER

*Attesting Officer*   *Acting Commissioner of Patents and Trademarks*